United States Patent [19]
Cahiez et al.

[11] Patent Number: 5,091,597
[45] Date of Patent: Feb. 25, 1992

[54] MANUFACTURE OF TERTIARY AND SECONDARY ALCOHOLS BY THE ACTION OF AN ORGANO-METALLIC COMPOUND ON A COMPOUND CARRYING A CARBONYL GROUP

[75] Inventors: Gérard Cahiez; Pierre-Yves Chavant, both of Paris; Pierre Tozzolino, Serres-Morlaas, all of France

[73] Assignee: Societe Nationale Elf Aquitaine, France

[21] Appl. No.: 574,374

[22] Filed: Aug. 28, 1990

Related U.S. Application Data

[63] Continuation of Ser. No. 291,045, Dec. 24, 1988, abandoned.

[30] Foreign Application Priority Data

Dec. 30, 1987 [FR] France ................. 87 18353

[51] Int. Cl.$^5$ .................. C07C 29/14; C07C 29/143; C07C 29/136
[52] U.S. Cl. ..................... 568/878; 549/497; 260/410; 558/451; 560/179; 568/598; 568/807; 568/825; 568/828
[58] Field of Search ............. 568/878, 598, 825, 828, 568/807; 560/179; 549/497; 558/451

[56] References Cited

U.S. PATENT DOCUMENTS

| | | | |
|---|---|---|---|
| 3,579,575 | 5/1971 | Bouniot | 568/878 X |
| 3,631,179 | 12/1971 | Urry | 568/878 X |
| 3,706,809 | 12/1972 | Moroe et al. | 568/878 X |

OTHER PUBLICATIONS

"Les Organomanganeux: ultilisation en Synthese Organique" by G. Cahiez, L'Actualite Chimiqux, Sep. 1984, p. 27.
"Carbon-Carbon Bond Formations with Metallic Manganese" by T. Hiyama, et al., Chemistry Letters, pp. 1237-1238.

*Primary Examiner*—Joseph Paul Brust
*Attorney, Agent, or Firm*—Ostrolenk, Faber, Gerb & Soffen

[57] ABSTRACT

Process of preparation of secondary or tertiary alcohols by the action of an organic halide on metallic manganese, in the presence of a carbonyl compound in a solvent followed by hydrolysis; a compound of a metal of Groups II to VIII of the Periodic Classification of the Elements, less electropositive than manganese, is present in the reaction medium.

18 Claims, No Drawings

MANUFACTURE OF TERTIARY AND SECONDARY ALCOHOLS BY THE ACTION OF AN ORGANO-METALLIC COMPOUND ON A COMPOUND CARRYING A CARBONYL GROUP

This is a continuation of application Ser. No. 07/291,045, filed Dec. 24, 1988, and now abandoned.

The present invention relates to an improvement in the preparation of secondary and tertiary alcohols. It relates especially to the preparation of such alcohols by the action of an organo-manganous compound on a compound carrying a carbonyl group.

The utility of secondary and tertiary alcohols is well known in the synthesis of natural products; among standard methods for their preparation, those based on the use of organo-metallic reactants are very interesting because they allow the preparation of various types of tertiary alcohols, especially useful in the pharmaceutical field, as well as those relating to aromas and perfumes. The route using organo-metallic compounds has been the subject of various studies, including amongst others those of Barbier ("C.R. Acad. Sci. Paris", Vol. 128, p. 110, 1899) which describes the preparation of alcohols starting with halides, magnesium and carbonyl compounds. This reaction is a modification of that of Wagner and Saytzeef ("Justus Liebigs Ann. Chem.", Vol. 175, p. 351, 1875) utilising zinc and forming the origin of the remarkable development of organo-magnesium chemistry. The use of zinc has been the subject of important studies; it concerns in particular the reaction of an α-bromoester and a carbonyl compound in the presence of zinc. This reaction is generally called the Reformatsky reaction.

Recent studies describe this same type of reaction, starting from various metals such as tin, cerium and Zn/Cu, Zn/Cd and Zn/Pb couples in the Reformatsky reaction.

A very clear advance has been realised in this area by the use of organo-manganous compounds, the advantage of which lies in their selectivity during attack on multi-functional molecules. Thus according to G Cahiez ("L'Actualité Chimique", September 1984, p. 27) the organo-manganous compounds react, like numerous organo-metallic compounds, with aldehydes and ketones to lead to tertiary alcohols, but they do not attack esters. This selectivity is interesting because it is total, even at ambient temperature.

Up to a recent period, organo-manganous derivatives were obtained by metal-metal exchange starting with lithium and magnesium compounds. This method of preparation precludes access to functional organo-manganous compounds such as X—MnCH$_2$—CO$_2$Et alone, because the lithium or magnesium starting compound cannot be obtained. This shows the advantage of preparing organo-manganous compounds directly from metallic manganese and an organic halide. Recently, Hiyama et coll. ("Organometallics" 1982, 1, 1249-1251) describe the reactivity of manganese metal obtained by reduction with the aid of the hydride LiAlH$_4$ of manganese chloride (II) with respect to allyl bromides; the reactant obtained, treated by an aldehyde or a ketone, leads to the corresponding tertiary alcohol. According to a later publication ("Chemistry Letters", p. 1237-38, 1983), the use of micronised manganese is economically very interesting. However, the attainment of good yields necessitates the use of excessive quantities of the reactants; metal/ketone or aldehyde ratios=7/1, halide/ketone or alcohol=6. Moreover, the reaction requires 1 eq. of iodine for a reflux for a dozen hours. This thus concerns an array of conditions which render the industrial exploitation of such syntheses very hypothetical.

The present invention provides a new solution which allows the production of all kinds of secondary or tertiary alcohols by the action of an organic halide, metallic manganese and an organic compound carrying a carbonyl, at temperatures around the ambient, and under good economic conditions. The invention allows in effect the production of the desired alcohols more rapidly and in better yields than has been possible according to the prior art.

The process according to the invention, which consists in reacting an organic halide with an organic compound, carrying at least one carbonyl group within an organic solvent, in the presence of metallic manganese and then hydrolysing the product formed, is characterised in that the reaction with the manganese is initiated and activated by addition to the reaction medium of certain metallic compounds of Groups II to VIII of the Periodic Classification of the Elements, less electropositive than manganese.

Thus, the reaction is accelerated by the addition to the medium in the organic solvent of a salt or an organic combination of a metal such as for example Zn, Cd, Sn, Hg, etc. This salt is an anion such that its solubility is sufficient in the medium and so that it can react with the metallic manganese (formation of the metal/metal couple). Zinc chloride has shown itself to be particularly active and economical.

Depending upon the nature of the reactants present, that of the physical structure of the Mn and the metallic salt employed, the proportion thereof can vary between wide limits, in particular between 10 and 200% molar with respect to the Mn and more particularly between 30 and 150% in molar equivalents with respect to the metal. To a certain extent, the yield of alcohol to be produced increases with the proportion of the activating metallic salt employed.

While the process of the invention is preferably carried out with the activating metal salt, dissolved in the solvent utilised, it can nevertheless be carried out with partially soluble salts maintained in dispersion, for example by continuous agitation of the medium with the manganese.

The particle size range of the manganese employed is from 1 to 2000 microns and preferably ranges between 10 and 500 microns. It is even possible, for preparations on a much larger scale, to use particle sizes greater than 2000 microns.

The solvents utilisable in the process of the invention can be selected from all of those which are compatible with the reactants present. Use can be made of certain ethers, such as THF or dimethoxyethane; equally convenient are esters, which have not been employed up till now, in particular acetates, propionates, etc. of methyl, ethyl and others, preferably having in total only 3 to 10 carbon atoms. Use can also be made of certain nitriles, such as acetonitrile or amides such as DMF. Tetrahydrofuran already utilised in the prior art is perfectly suitable.

Various co-solvents can be used with the solvents cited such as halogenated solvents, particularly methylene chloride, chlorobenzene, trichloroethane, chloroalkanes or aliphatic or aromatic hydrocarbons.

The assembly of the reactions which form the process of the invention can be represented in the following manner:

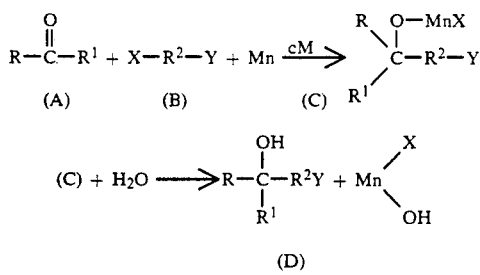

$$(C) + H_2O \longrightarrow R-\underset{\underset{R^1}{|}}{\overset{\overset{OH}{|}}{C}}-R^2Y + Mn\diagup^{X}_{OH} \quad (2)$$

(D)

The reaction (1) takes place within a solvent in which the two reactants (A) and (B) preferably are soluble. The principle of the invention resides in the addition of an activating compound "cM" of a metal less electropositive than Mn, as explained above.

The organo-manganous compound (C) can be separated from the reaction medium, in order to be subjected to hydrolysis (2); in particular the solvent can be evaporated after the reaction (1) and the residue treated with water in a manner known per se. Hydrolysis can also take place directly in the solvent after reaction (1). It is in general effected in acid medium and the Mn is recovered in the form of its salt $MnX_2$.

The compound (A) is an aldehyde when $R^1$ is H or a ketone when R and $R^1$ are hydrocarbon groups; these can be aliphatic, preferably from $C_1$ to $C_8$, cyclo-aliphatic, especially from $C_4$ to $C_8$, and/or aryl, particularly phenyls or napththyls which can carry alkyl, alkenyl, halogen or other substituents.

R in the case of an aldehyde and R and/or $R^1$ in the case of a ketone can carry functions such as ester, nitrile, ether, sulphide, halide and acetal.

Thus the reactant (A) can be for example such as acetaldehyde, propionaldehyde, butyraldehyde, phenylacetaldehyde, benzaldehyde, cinnamic aldehyde, anisaldehyde, etc.

It can be constituted by a ketone of the acetone type, dipropylketone, methylethylketone, methylheptenone, cyclopentanone, methylcyclohexanone, methyl acetylpropionate, acetophenone, benzophenone, menthone, naphthylmethylketone, etc.

In the organic halide (B), X designates a halogen, especially Br. $R^2$ is a hydrocarbon group; Y represents a functional group, its presence not being obligatory. On the other hand, the organic halide can be allyl, propargyl, benzyl or an α-halogen-ester or nitrile. Thus the compound (B) can be for example, $Br-CH_2-CH=CH_2$; $Cl-CH_2-CH=CH_2$; $Br-CH_2-C_6H_5$; $Br-CH_2-C(CH_3)=CH_2$; $Br-CH_2-CO_2Et$; $I-CH_2-CH=C(CH_3)_2$ or others.

The substances cited above only constitute non-limitative examples of the compounds (A) and (B) and are given as a guide.

The process according to invention can be carried out with stoichiometric ratios of the reactants (A), (B) and Mn in the reaction (1). However, it has proved preferable to operate with a certain excess of the metal Mn and of the compound (B) with respect to the carbonyl compound (A). In effect, the yields of secondary or tertiary alcohol are increased when Mn and (B) are in excess with respect to stoichiometry. In a general manner, it is useful to employ 1 to 3 atoms of Mn and 1 to 2 moles of (B) per mole of the carbonyl compound (A).

The preferred proportions range between 1.2 and 1.6 atoms of Mn and 1.1 and 1.5 moles of the halide (B).

On the other hand, it is advantageous to work with solutions which are sufficiently but not too concentrated of the compound (A) particularly 0.3 to 2M solutions and preferably 0.5 to 1.6M.

The temperature during stage (1) of the process can range between 20° and 100° C., the range from 30° to 60° C. being preferable.

Addition of the reactants should be effected over a time which in general is of the order of 1 to 6 hours and most frequently from 3½ to 4½ hours; this constitutes a marked advantage over the prior technique, which requires about 12 hours or more. Due to the addition of the metallic activator salt, the reaction starts immediately, while it only starts after about 2 hours in the known process using Mn powder.

The invention is illustrated by the non-limitative examples given below, in which the following mode of operation is employed.

The reactor comprises a 3-necked flask of 100 ml capacity, provided with a mechanical agitator, mounted so as to cause movement of the Mn powder which is placed in the reactor. This also comprises a thermometer and a nitrogen input tube allowing an inert atmosphere to be established in the apparatus, throughout the operations. The reactor is placed in a water bath maintained at the desired temperature.

The manganese is 98-99% coarse powder having a particle size ranging between 10 and 500 microns. It is charged to the flask with the metal activator salt and covered with the solvent. The reaction is initiated by several drops of the organic halide (B), $XR^2Y$; as soon as the metal has undergone a change of colour and when heating has been produced, progressive introduction of the reactants (A) and (B) is begun with the aid of pumps. At the end of this introduction, which lasts several hours, agitation of the medium is continued for 15 to 30 mn at the same temperature which has been used for reaction (1). Then the reaction medium is mixed with approximately its own volume of water at 20° C., slightly acidified with HCl in order to modify the pH of the water to 7 or to a slightly lower value, in order to dissolve the metallic salts present. The desired product is extracted with ether and washed with Na bicarbonate. The yield of the alcohol obtained with respect to the compound (A) is calculated from the quantity of alcohol isolated by extraction and distillation.

EXAMPLES 1 AND 2

Preparation of 4-allyl-heptanol-4 comparatively according to the prior art and according to the invention Operating as indicated above, 1 mole of dipropylketone $CH_3CH_2CH_2-CO-CH_2CH_2-CH_3$ is reacted with 1.1 mole of allyl bromide $CH_2=CH-CH_2Br$ and 1.3 atoms of metal powder Mn in well-dried tetrahydrofuran in the proportion of 0.7 liter of this solvent for the quantities indicated. The reaction takes place at 60° C. for 4 hours.

EXAMPLE 1

Nothing else is added to the reaction medium. At 60° C., the reaction has not started after 6 hours. Analysis of the reaction medium does not allow formation of the expected product to be demonstrated.

EXAMPLE 2

To the reaction medium described above, there is first added 2.7 g of $ZnCl_2$ per liter of solution or 0.02 mole. The reaction starts as soon as introduction of the reactants is commenced. The yield of tertiary alcohol after 4 hours at 60° C. is 77% with respect to the dipropyl-ketone. Activation by the zinc chloride is thus remarkable.

EXAMPLE 3

Influence of the proportion of the metal activating salt 6-allyl-undeconal-6:

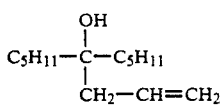

is prepared as in Example 2, but by replacing the dipropylketone with dipentyl-ketone $(C_5H_{11})_2CO$ and the bromide by allyl bromide.

With different proportions of $ZnCl_2$ added per mole of ketone, the following yields have been found for dipentyl-ketone, determined from the tertiary alcohol formed and isolated.

| Moles $ZnCl_2$ per mole of Ketone | Yield % |
|---|---|
| 0.02 | 85% |
| 0.05 | 89 |
| 0.10 | 90 |
| 0.15 | 95 |

EXAMPLE 4

Role of temperature

Example 2 is repeated at three different temperatures for the first stage of the preparation, the concentration of the dipropyl-ketone being 1.33M in tetrahydrofuran. The yields of the ketone determined by chromatography are:

| for 50° C. | 60% |
|---|---|
| 60° C. | 77 |
| 70° C. | 85 |

EXAMPLE 5

Influence of the proportions of the reactants

Preparations identical with those of Example 4 are effected with variable proportions of the bromide (B) and of Mn. They led to the following yields indicated by vapour phase chromatography.

| Moles $CH_2=CH-CH_2Br$ per mole of Ketone | Atoms Mn per mole Ketone | Yield % |
|---|---|---|
| 1.1 | 1.3 | 77% |
| 1.3 | 1.4 | 84 |
| 1.4 | 1.5 | 90 |

EXAMPLE 6

Effect of concentration of compound (A)

By repeating Example 2 with variable molar concentrations of dipropyl-ketone (compound A), the following yields have been found:

| Concentration of (A) in the reaction medium | Yield % |
|---|---|
| 0.67 M | 76% |
| 1.33 | 79 |
| 1.70 | 75 |

There is thus a certain optimum.

EXAMPLE 7

By replacing in Example 5 the allyl bromide with the chloride (1.1 mole) and adding 0.1 mol $ZnCl_2$ in place of 0.02 mol per mole of dipropyl-ketone, the following yields have been attained:

| 81% with 1.3 gram-atoms Mn/mole Ketone |
|---|
| and 94% with 1.8 gram-atoms Mn/mole Ketone |

EXAMPLE 8

Use of a ketone-ester

Under the general conditions of Example 2, 1 mole of methyl 8-oxo-dodecanoate is reacted with allyl chloride in the presence of Mn and 0.1 mole of $ZnCl_2$ at 60° C. for $4\frac{1}{4}$ hours. The following was obtained according to the reaction:

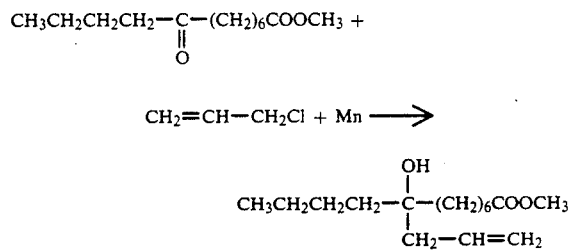

The yield of this tertiary alcohol with an unsaturated group and an ester group is 67% over the initial ketone, when using 1.3 mole of allyl chloride with 1.5 atom of Mn. 76% can be achieved by employing 1.6 mole of the chloride and 1.6 atom of Mn. This preparation gives very poor results if the medium does not include a metal salt, particularly $ZnCl_2$; thus the invention allows the easy preparation of alcohols carrying two other functions.

EXAMPLE 9

Use of aldehydes

Following the mode of operation of Example 2 at 60° C., 1 mole of hexyl-aldehyde (normal heptanal) was reacted with 1.3 mole of allyl chloride and 1.3 atom of Mn, the concentration of the aldehyde in tetrahydrofuran being 0.67M. The activator. $ZnCl_2$ was present in the ratio of 0.1 mole per mole of aldehyde.

After 4 hours 10 minutes, the yield of secondary alcohol

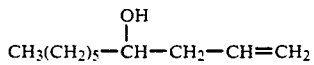

$$CH_3(CH_2)_5-\overset{OH}{\underset{|}{CH}}-CH_2-CH=CH_2$$

was 85% with respect to the initial aldehyde.

EXAMPLE 10

Use of an ester function halide

The mode of operation above was used for the reaction

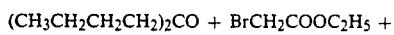

$(CH_3CH_2CH_2CH_2)_2CO + BrCH_2COOC_2H_5 +$

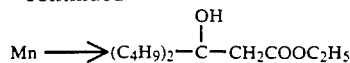

$$Mn \longrightarrow (C_4H_9)_2-\overset{OH}{\underset{|}{C}}-CH_2COOC_2H_5$$

and led to a yield of 23%.

EXAMPLES 11 TO 24

In the accompanying table the yields of secondary or tertiary alcohol are given for several preparations carried out starting from various carbonyl compounds (A) and organic halides (B). The formulae of these compounds as well as the proportions of (B) and of Mn per mole of (A) are also indicated. The temperature was 60° C., the quantity of zinc chloride was 0.1 mole per mole of (A) and the duration was 4 hours to 4½ hours. The solvent was THF (see tables on following pages).

TABLE SUMMARISING EXAMPLES 11 TO 24

| Ex. no. | Compound (A) | Halide (B) | Mn | Yield % | Alcohol obtained |
|---|---|---|---|---|---|
| 11 | (CH₃)₂HC—CO—CH(CH₃)₂ | ClCH₂—CH=CH₂  1.3 | 1.3 | 78 | (CH₃)₂CH—C(OH)(CH₂—CH=CH₂)—CH(CH₃)₂ |
| 12 | (CH₃O)₂CH—CH₂—CO—CH₃ | ClCH₂—CH=CH₂  1.3 | " | 77 | (CH₃O)₂CH—C(OH)(CH₃)—CH₂—CH=CH₂ |
| 13 | tetrahydrothiopyran-4-one | ClCH₂—CH=CH₂  1.3 | 1.5 | 81.5 | 4-hydroxy-4-allyl-tetrahydrothiopyran |
| 14 | 4,4,6-trimethyl-cyclohex-5-en-1-one | ClCH₂—CH=CH₂  1.3 | 1.3 | 94 | 1-hydroxy-1-allyl-4,4,6-trimethyl-cyclohex-5-ene |
| 15 | 4-bromoacetophenone | ClCH₂—CH=CH₂  1.3 | 1.5 | 76 | 4-bromo-α-methyl-α-allyl-benzyl alcohol |
| 16 | Cl(CH₂)₅—CO—(CH₂)₃CH₃ | ClCH₂—CH=CH₂  1.3 | 1.3 | 93 | Cl(CH₂)₅—C(OH)[(CH₂)₃CH₃](CH₂—CH=CH₂) |
| 17 | (CH₃)₂C=CH—CH₂CH₂—C(CH₃)=CH—CHO | CH₂=CH—CH₂Cl  1.3 | 1.3 | 80 | (CH₃)₂CH=CH—(CH₂)₂—C(CH₃)=CH—CH(OH)—CH₂—CH=CH₂ |
| 18 | furan-2-carbaldehyde | CH₂=CH—CH₂Cl  1.3 | " | 94 | furan-2-yl—CH(OH)—CH₂—CH=CH₂ |
| 19 | benzaldehyde | CH₂=CH—CH₂Cl  1.3 | 1.7 | 90 | phenyl—CH(OH)—CH₂—CH=CH₂ |

TABLE SUMMARISING EXAMPLES 11 TO 24 -continued

| Ex. no. | Compound (A) | Halide (B) | Mn | Yield % | Alcohol obtained |
|---|---|---|---|---|---|
| 20 | C6H5—CHO | C6H5—CH2Cl  1.4 | 1.5 | 88 | $C_6H_5-CH(OH)-CH_2C_6H_5$ |
| 21 | $CH_3(CH_2)_3CHO$ | cyclohexenyl-Cl  1.3 | 1.3 | 85 | $CH_3(CH_2)_3CH(OH)-$cyclohexenyl |
| 22 | $CH_3(CH_2)_5CHO$ | $Br-C(CH_3)_2-CH=CH_2$  1.3 | 1.5 | 76 | $CH_3(CH_2)_5CH(OH)-C(CH_3)_2-CH=CH_2$ |
| 23 | $(CH_3O)_2CHCH_2COCH_3$ | $ClCH_2C(CH_3)=CH_2$  1.3 | 1.3 | 95 | $(CH_3O)_2CHCH_2C(OH)(CH_3)-CH_2C(CH_3)=CH_2$ |
| 24 | $Cl(CH_2)_5CO(CH_2)_3CH_3$ | $ClCH_2CH=CH_2$  1.3 | 1.3 | 93 | $Cl(CH_2)_5C(OH)(CH_2CH=CH_2)-(CH_2)_3-CH_3$ |

EXAMPLES 25 to 32

Preparations similar to those of Example 2 starting from dipropylketone $(C_3H_7)_2CO$ were carried out with different organic halides and in different solvents. Also, the zinc salt was replaced with cadmium, mercury or tin salts. The characteristics of these tests are as follows:

| Test No. | Halide | Metal compound | | Solvent |
|---|---|---|---|---|
| 25 | $(CH_3)_2C=CH-CH_2Cl$ | $HgCl_2$ | 0.1 mole | THF |
| 26 | " | $HgCl_2$ | 0.05 mole | Ethyl Acetate |
| 27 | " | $CdCl_2$ | 0.1 mole | THF |
| 28 | " | $SnCl_4$ | 0.1 mole | THF |
| 29 | $C_6H_5CH_2Cl$ | $HgCl_2$ | 0.1 mole | THF |
| 30 | " | $CdCl_2$ | 0.1 mole | THF |
| 31 | $CH_2=C(CH_3)CH_2Br$ | $HgCl_2$ | 0.1 mole | THF |
| 32 | " | $ZnCl_2$ | 0.05 mole | Ethyl Acetate |

The yields are of the same order as those of Example 2.

We claim:

1. In the process of preparing a secondary or tertiary alcohol by reacting an aldehyde or ketone of the formula $RCOR^1$ where R is an alkyl, alkenyl, cycloalkyl, phenyl or naphthyl group optionally substituted by a group which forms therewith an ester, nitrile, ether, sulfide, halide or acetal and $R^1$ is hydrogen or selected from the same groups consisting R, with an organic halide $XR^2(Y)_{0-1}$ where X is halogen, $R^2$ is a hydrocarbon group and Y represents a $-COOC_2H_5$ nitrile or amide group in an organic solvent and in the presence of powdered metallic manganese at a temperature of 20° to 100° C., hydrolyzing the product obtained as a result of the reaction and separating the secondary or tertiary alcohol thus produced, the improvement which comprises conducting the reaction in the presence of 0.01 to 2 equivalents per gram-atom of manganese of an activator which is a chloride, bromide or iodide of zinc, cadmium, mercury or tin in the reaction medium.

2. The process of claim 1 in which the amount of activator is 0.3 to 1.5 equivalents per gram-atom of manganese.

3. The process of claim 2 in which one mol of aldehyde or ketone is reacted with 1 to 2 mols of the organic halide and 1 to 3 gram-atoms of the metallic manganese.

4. The process of claim 3 in which the temperature is 50° to 80° C.

5. The process of claim 4 in which the concentration of aldehyde or ketone in the solvent is 0.3 to 2M.

6. The process of claim 5 in which the concentration is 0.5 to 1.6M.

7. The process of claim 5 in which the aldehyde or ketone is an aldehyde selected from the group consisting of acetaldehyde, propionaldehyde, butyraldehyde, phenylacetaldehyde, benzaldehyde, cinnamic aldehyde and anisaldehyde.

8. The process of claim 5 in which the aldehyde or ketone is an aldehyde selected from the group consisting of dipropylketone, methylethylketone, methylheptenone, cyclopentanone, methylcyclohexanone, methyl acetyl propionate, acetophenone, benzophenone, menthone and naphtylmethylketone.

9. The process of claim 5 in which the activator is zinc chloride.

10. The process of claim 1 in which the solvent is an ether, a nitrile, an amide or a mixture thereof with a chlorinated solvent or an aliphatic or aromatic hydrocarbon.

11. The process of claim 1 in which the solvent is ethyl acetate.

12. In the process of preparing a secondary or tertiary alcohol by reacting an aldehyde or ketone of the formula $RCOR^1$ where R is a 1 to 8 carbon atoms alkyl or alkenyl group, a 4 to 8 carbon atom cycloalkyl group, phenyl or napthyl and $R^1$ is hydrogen or selected from the same groups constituting R with an organic halide $XR^2Y$ in which X is halogen, $R^2$ is a hydrocarbon group having up to 5 carbon atoms or benzyl and Y is H or $-COOC_2H_5$ in an organic solvent and in the presence of powdered metallic manganese at a temperature of 20° to 100° C. and hydrolyzing the product obtained as a result of the result, the improvement which comprises conducting the reaction in the presence of 0.01 to 2 equivalents per gram-atom of manganese of an activator which is a chloride, bromide or iodide of zinc in the reaction medium.

13. The process of claim 12 in which the amount of activator is 0.3 to 1.5 equivalents per gram-atom of manganese.

14. The process of claim 13 in which one mol of aldehyde or ketone is reacted with 1 to 2 mols of the organic halide and 1 to 3 gram-atoms of the metallic manganese.

15. The process of claim 14 in which the temperature is 50° to 80° C.

16. The process of claim 15 in which the concentration of aldehyde or ketone in the solvent is 0.3 to 2M.

17. The process of claim 16 in which the concentration is 0.5 to 1.6M.

18. The process of claim 1 in which the activator is zinc chloride.

* * * * *